United States Patent
Arnold et al.

(10) Patent No.: US 10,456,226 B2
(45) Date of Patent: Oct. 29, 2019

(54) TOOTH REPLACEMENT

(71) Applicants: Wolfgang Arnold, Essen (DE); Volker Brosch, Essen (DE)

(72) Inventors: Wolfgang Arnold, Essen (DE); Volker Brosch, Essen (DE)

(73) Assignee: KUZLER GMBH, Hanau (DE)

( * ) Notice: Subject to any disclaimer, the term of this patent is extended or adjusted under 35 U.S.C. 154(b) by 17 days.

(21) Appl. No.: 15/596,554

(22) Filed: May 16, 2017

(65) Prior Publication Data
US 2017/0319306 A1    Nov. 9, 2017

Related U.S. Application Data

(63) Continuation of application No. 14/232,881, filed as application No. PCT/EP2012/002987 on Jul. 16, 2012, now abandoned.

(30) Foreign Application Priority Data

Jul. 14, 2011    (DE) .................... 20 2011 103 184 U

(51) Int. Cl.
 *A61C 13/097*    (2006.01)
 *A61C 13/08*    (2006.01)
(52) U.S. Cl.
 CPC ............ *A61C 13/097* (2013.01); *A61C 13/08* (2013.01)
(58) Field of Classification Search
 CPC .............................. A61C 13/08; A61C 13/097
(Continued)

(56) References Cited

U.S. PATENT DOCUMENTS

RE23,607 E  * 12/1952  Donavan ............... A61C 13/097
                                                             433/198
2,620,562 A  * 12/1952  Folsom ................ A61C 13/097
                                                             433/197
(Continued)

FOREIGN PATENT DOCUMENTS

| DE | 10163105 A1 | 7/2003 |
| EP | 1010402 B1 | 9/2003 |
| WO | WO2009044443 A1 | 1/2011 |

OTHER PUBLICATIONS

English Translation of International Search Report dated May 7, 2013 for International Application No. PCT/2012/002987, 2 pages.

(Continued)

*Primary Examiner* — Wade Miles
*Assistant Examiner* — Matthew P Saunders
(74) *Attorney, Agent, or Firm* — Shwabe, Williamson & Wyatt, P.C.

(57) ABSTRACT

The invention relates to a tooth replacement including at least one posterior tooth having a mesial contact surface, a distal contact surface, and an occlusal surface. The occlusal surfaces includes at least one buccal cusp having a buccal cusp tip, a lingual cusp having a lingual cusp tip, a central fissure which has at least one tooth pit and passes through the occlusal surface in the mesiodistal direction between the two cusps, a first gradient which slopes downward from the buccal cusp tip in the direction of the central fissure, and a second gradient which slopes downward from the lingual cusp tip in the direction of the central fissure. The tooth replacement according to the invention is characterized in that the mesial contact surface, the distal contact surface and/or the occlusal contact surface comprise expansion spaces that have been incorporated in a targeted manner to obtain a dynamic occlusal guidance.

17 Claims, 13 Drawing Sheets

(58) Field of Classification Search
USPC .................................................. 433/147, 171
See application file for complete search history.

(56) References Cited

U.S. PATENT DOCUMENTS

| | | | | |
|---|---|---|---|---|
| 3,277,575 | A * | 10/1966 | Stasiw | A61C 13/097 433/198 |
| 4,445,863 | A | 5/1984 | Lang et al. | |
| 4,626,215 | A * | 12/1986 | Clarke | A61C 13/097 433/198 |
| 5,326,262 | A | 7/1994 | Jorgenson | |
| 5,395,238 | A | 3/1995 | Andreiko et al. | |
| 5,733,125 | A * | 3/1998 | Foser | A61C 13/097 433/197 |
| 5,951,289 | A * | 9/1999 | Kura | A61C 13/097 433/197 |
| 6,508,651 | B1 * | 1/2003 | Nakamura | A61C 13/09 433/197 |
| 6,533,581 | B1 * | 3/2003 | Moenckmeyer | A61C 13/08 433/197 |
| 7,267,549 | B2 | 9/2007 | Mönkmeyer | |
| 8,128,404 | B2 | 3/2012 | Satoh et al. | |
| 8,403,669 | B2 * | 3/2013 | Satoh | A61C 5/70 433/197 |
| 8,758,014 | B2 | 6/2014 | Kadobayashi | |
| 9,173,724 | B2 | 11/2015 | Moriyama et al. | |
| 2004/0137407 | A1 * | 7/2004 | Lauciello | A61C 13/097 433/196 |
| 2005/0095559 | A1 * | 5/2005 | Monkmeyer | A61C 13/097 433/171 |
| 2010/0035208 | A1 | 2/2010 | Kadobayashi | |
| 2010/0040997 | A1 | 2/2010 | Kadobayashi | |
| 2010/0119992 | A1 | 5/2010 | Satoh et al. | |
| 2010/0151419 | A1 | 6/2010 | Kadobayashi et al. | |
| 2010/0151424 | A1 | 6/2010 | Kadobayashi et al. | |
| 2010/0266988 | A1 | 10/2010 | Satoh et al. | |
| 2011/0045441 | A1 | 2/2011 | Kadobayashi | |

OTHER PUBLICATIONS

International Preliminary Report for Application No. PCT/EP2012/002987 dated Jan. 23, 2014.
Non-Final Office Action dated May 5, 2016 for U.S. Appl. No. 14/232,881, 20 pages.
Final Office Action dated Nov. 18, 2016 for U.S. Appl. No. 14/232,881, 16 pages.

* cited by examiner 26  14

16

TOOTH REPLACEMENT

CROSS REFERENCE TO RELATED APPLICATION

The present application is a continuation of and claims priority under 35 U.S.C. § 120 to U.S. patent application Ser. No. 14/232,881, entitled "TOOTH REPLACEMENT", which is a national phase entry of, and claims priority under 35 U.S.C. § 120 to International Patent Application No. PCT/EP2012/002987, filed Jul. 16, 2012, which designates the United States of America and which claims priority to German Patent Application No. 20 2011 103 184.9 filed Jul. 14, 2011. The entire content and disclosure of which is hereby incorporated by reference in its entirety.

BACKGROUND

The invention relates to a tooth replacement comprising at least one posterior tooth having a mesial contact surface, a distal contact surface, and an occlusal surface wherein the occlusal surface comprises a least one buccal cusp having a buccal cusp tip, a lingual cusp having a lingual cusp tip, a central fissure which has at least one tooth pit and passes through the occlusal surface in the mesiodistal direction between the two cusps, a first gradient which slopes downward from the buccal cusp tip in the direction of the central fissure, and a second gradient which slopes downward from the lingual cusp tip in the direction of the central fissure.

Teeth are mainly used to crush food, but also to speak. The distinctive features of a tooth include the crown that protrudes from the gum out into the oral cavity, the tooth neck and the tooth root which may be split and which at one end has an opening for nerves. The transition between the tooth crown and the tooth root is referred to as the tooth neck.

The natural dentition which consists of upper and lower jaw consists of incisors, canine teeth and posterior teeth, i.e., the premolars and molars. The premolars are built lower and feature a two-cusped crown, the molars have broad, up to 5-cusped crown.

In tooth replacements, artificial tooth crowns, entire replacement teeth or full dentures to make sure of the masticatory function.

In the context of this invention, entire teeth and tooth crowns are referred to as teeth.

Removable tooth replacement is necessary then when a large part of the natural teeth is no longer present or even all teeth had to be removed. Today, such partial or full dentures mostly are made of plastic as a support material, in which the replacement teeth are embedded.

The common replacement teeth which are implemented in simplified form often cause unusual bite properties, wherein it is particularly unpleasant that the temporomandibular joint responds even to small deviations from the usual movement sequence, and at times also it is elected not to use the dentures for extended periods of time.

As a solution to these problems in the prior art, EP 1 010 402 B1 suggests a tooth replacement, wherein the replacement teeth are fitted with multi-functional occlusal surfaces like their real life counterparts, have an enlarged volume and have a buccally stepped tooth neck that prevents translucence of the tooth necks. Here, in theses known teeth, the cusps of the tooth crowns can have a slope that decreases from the premolars to the molars.

The disclosure of EP 1 010 402 B1 is hereby incorporated into this description in terms of the formation of the occlusal surfaces and cusp slope by express reference. The use of the teeth as described in the cited document leads in many cases to satisfactory bite characteristics. However, it has been found that these bite characteristics may be lost during the period of use of the known dentures.

BRIEF DESCRIPTION OF THE DRAWINGS

In the drawing:

FIGS. 1a-1b to 6a-6b, 8a-8e and 9a-9h show various views of a first embodiment of the tooth replacement according to the invention.

The expansion spaces that have been incorporated into the occlusal surfaces in a targeted manner according to the invention can be particularly clearly seen in the side views shown in FIGS. 3a-3b to 5a-5b and 8a-8e.

DETAILED DESCRIPTION

In view of the problems described in the prior art, the present invention seeks to provide an improved tooth replacement, which can ensure the desired bite characteristics reliably over a long period of time and which is established easily and clearly.

Figure 6A:
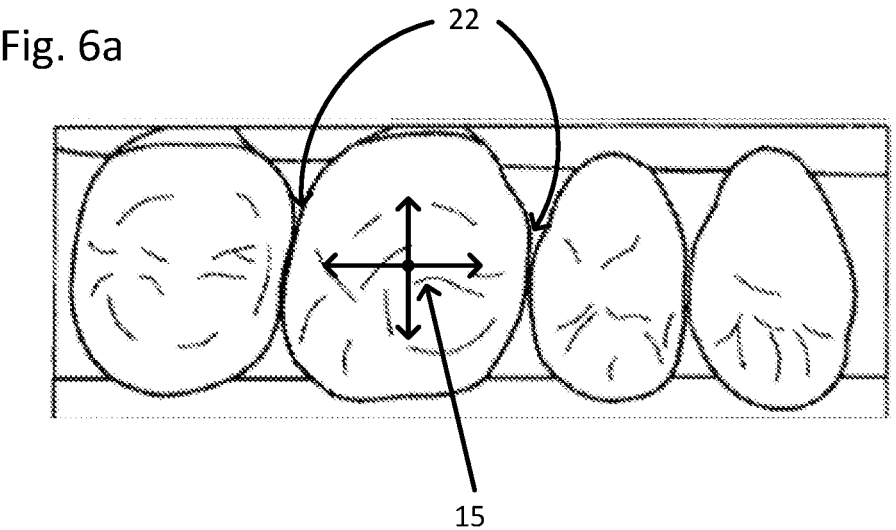
FIGS. 6a, 6b show the occlusal surfaces of the posterior teeth of the tooth replacement according to the invention.
Figure 9A:
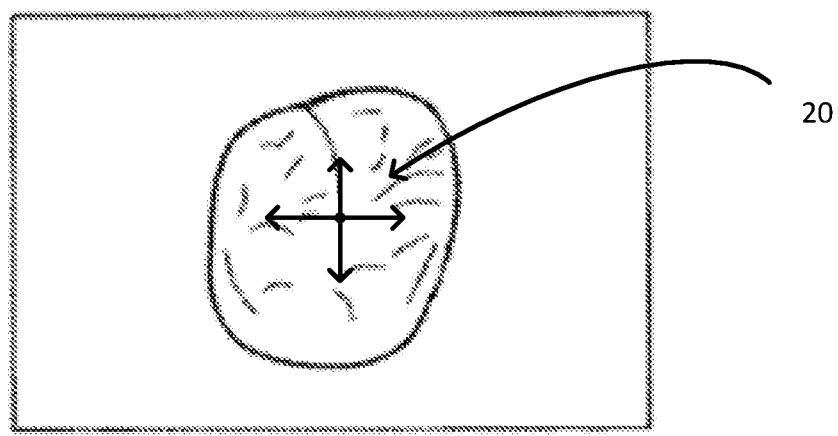
FIGS. 9a, 9b, 9c, 9d, 9e, 9f, 9g, 9h show the occlusal surfaces of the individual posterior teeth of the first embodiment of the tooth replacement according to the invention.
Figure 9B:
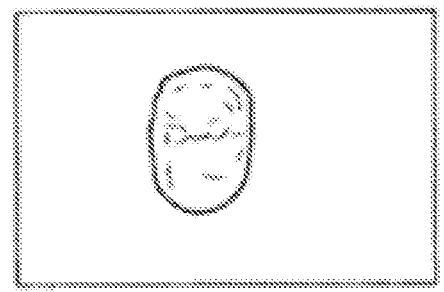
Figure 9C:
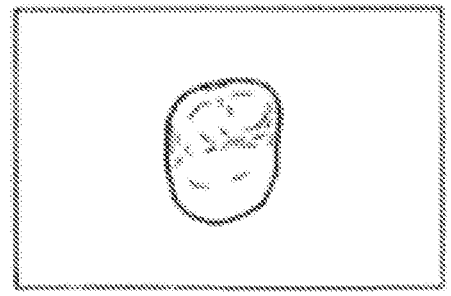
Figure 9D:
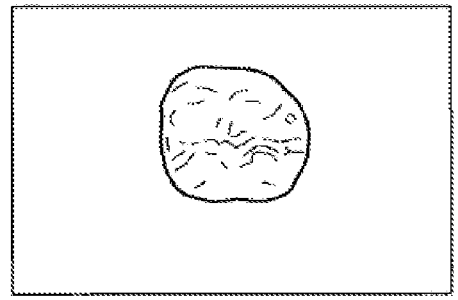
Figure 9E:
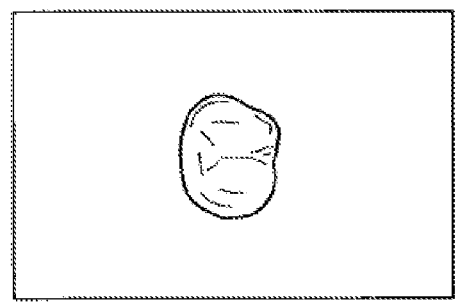
Figure 9F:
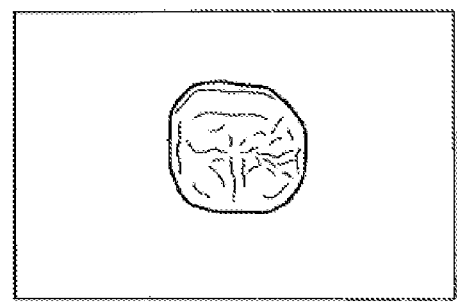
Figure 9G:
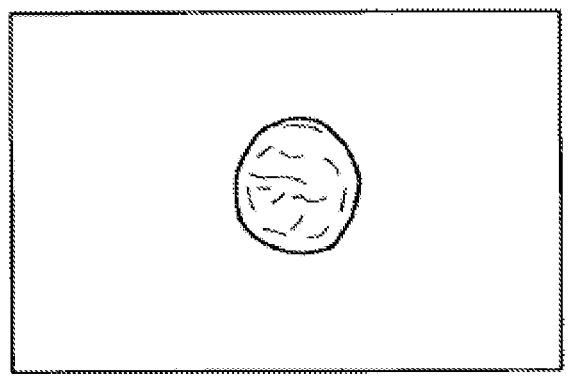
Figure 9H:
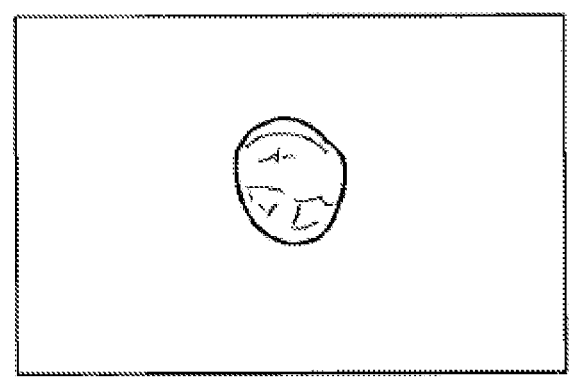

According to the invention this object is achieved by a refinement of the well-known tooth replacement that is essentially characterized in that the mesial contact surface, the distal contact surface and/or the occlusal contact surface comprise expansion spaces (15, FIG. 6a, 20, FIG. 9a) that have been incorporated in a targeted manner to obtain a dynamic occlusal guidance.

Advantageous embodiments of the invention are illustrated in the dependent claims.

Figure 1A:
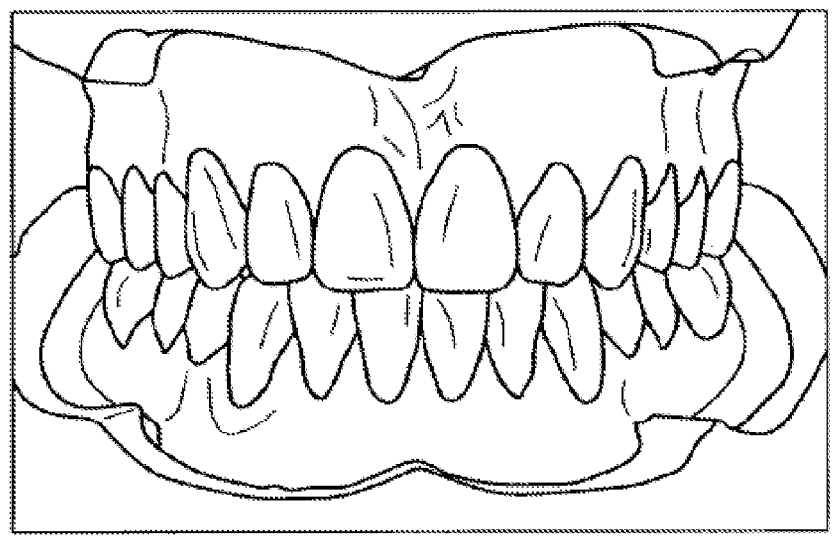
FIGS. 1a, 1b show an embodiment of the tooth replacement according to the invention from the front (FIG. 1a) and from the back (FIG. 1b)
Figure 1B:
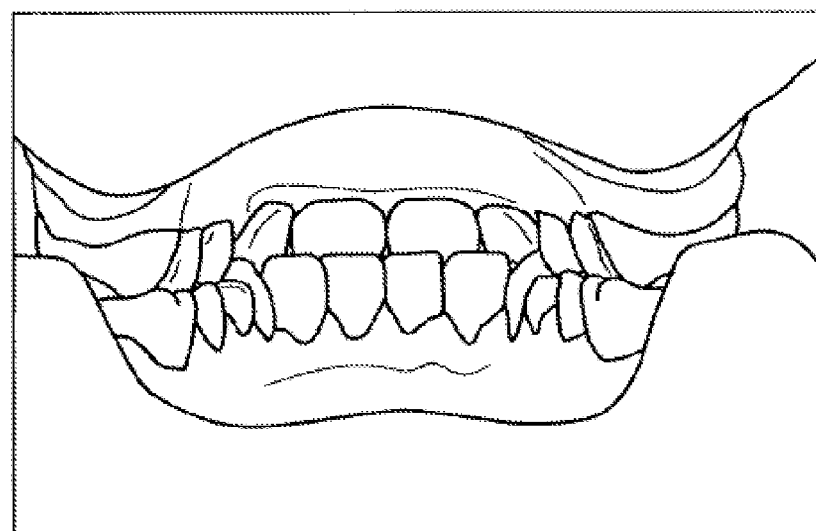
Figure 2A:
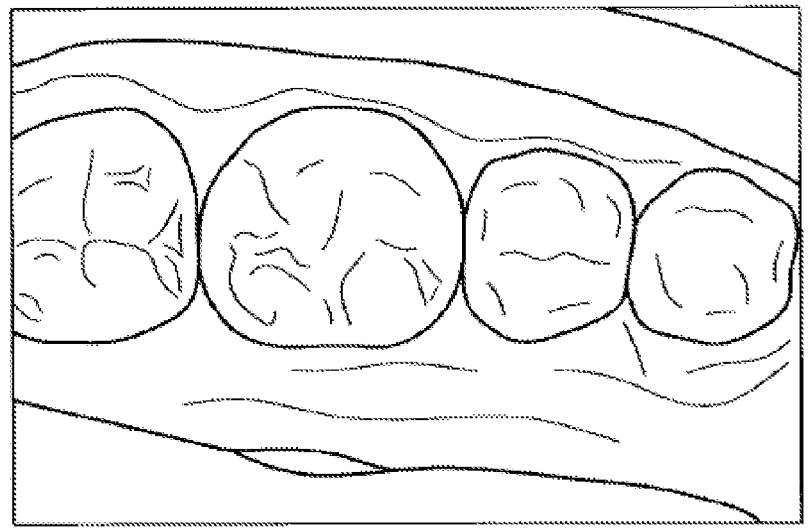
FIGS. 2a, 2b, 2c, 2d, 2e show the occlusal surfaces of posterior teeth (molars and premolars) of the tooth replacement according to the invention.
Figure 2B:
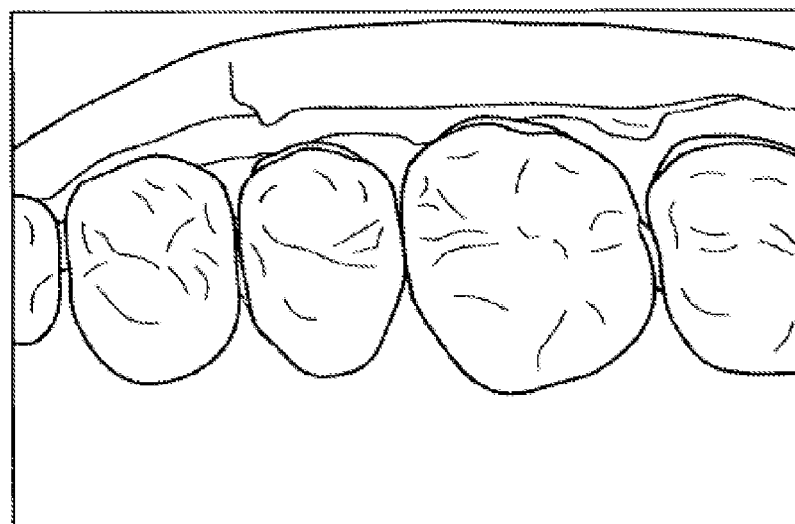
Figure 2C:
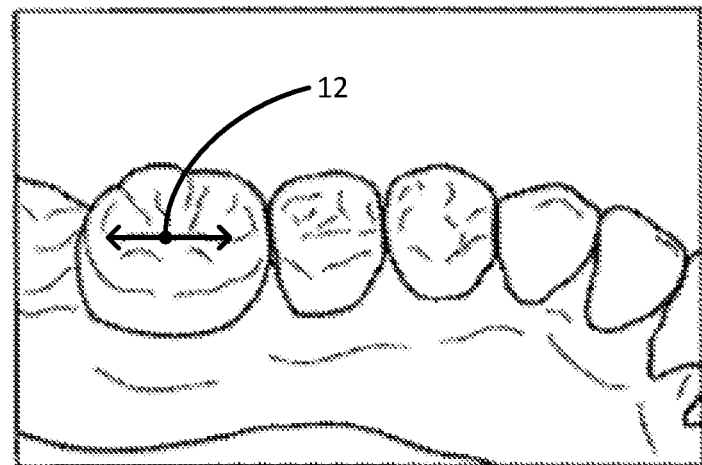
Figure 2D:
Figure 2E:
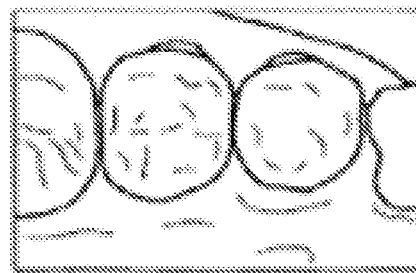
Figure 3A:
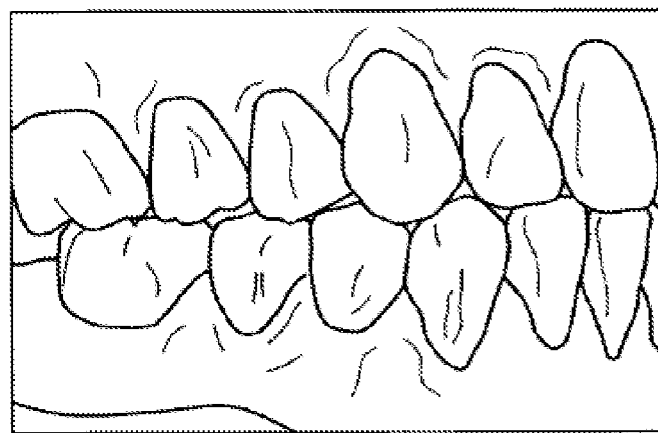
FIGS. 3a, 3b show side views of the left and right side of the jaw in the "neuronal contact position"
Figure 3B:
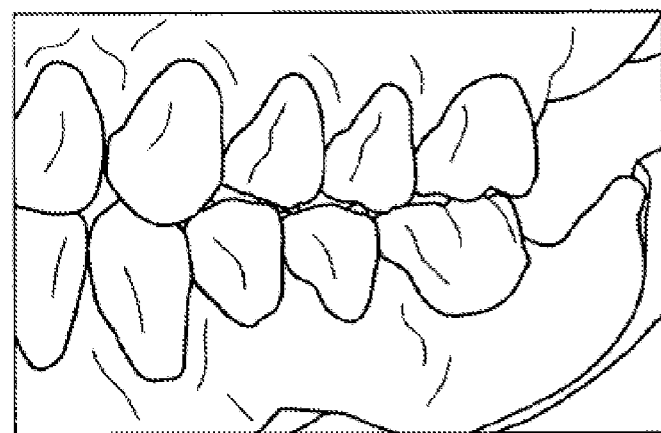
Figure 4A:
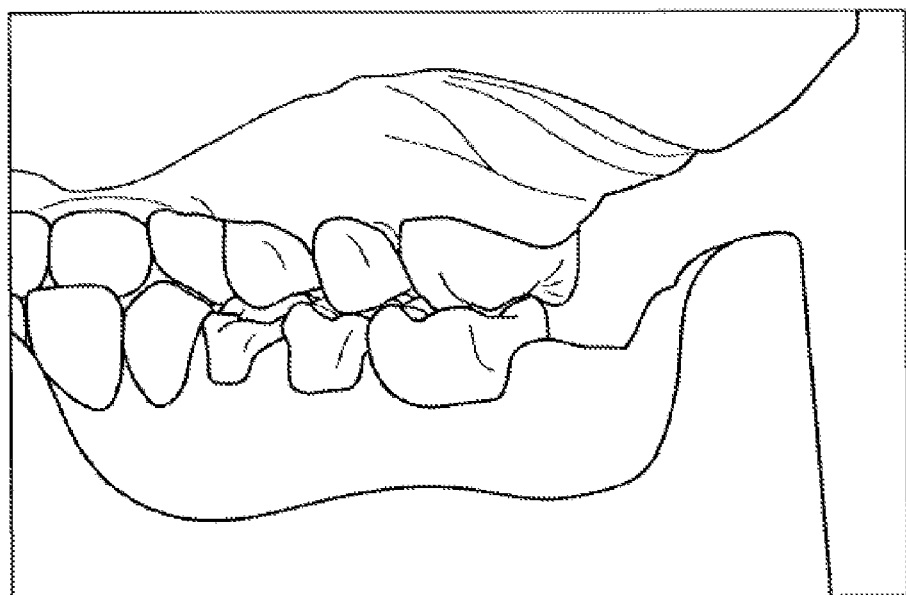
FIGS. 4a, 4b show a view of the right half of the jaw from dorsal both in the phase of the closing of the jaw (FIG. 4a) and in the closed position (FIG. 4b)
Figure 4B:
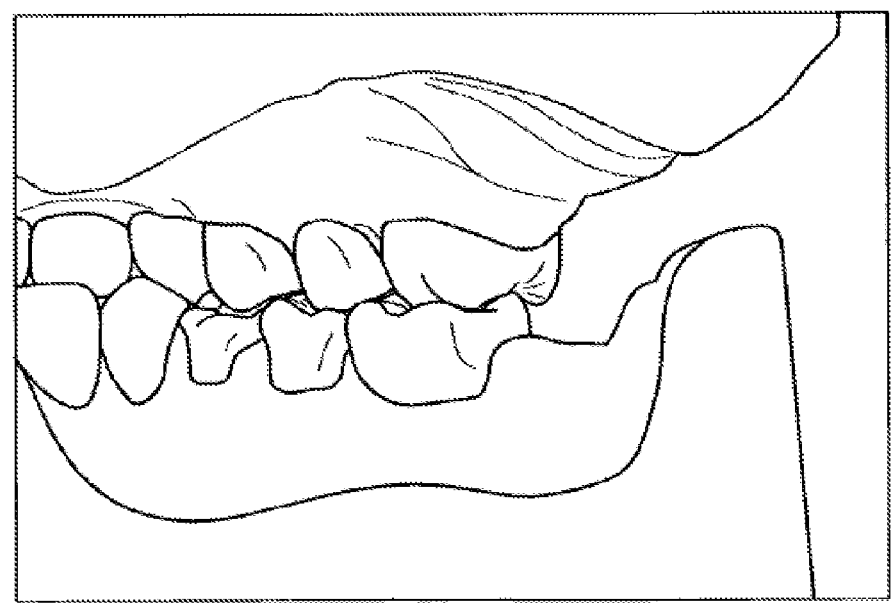
Figure 5A:
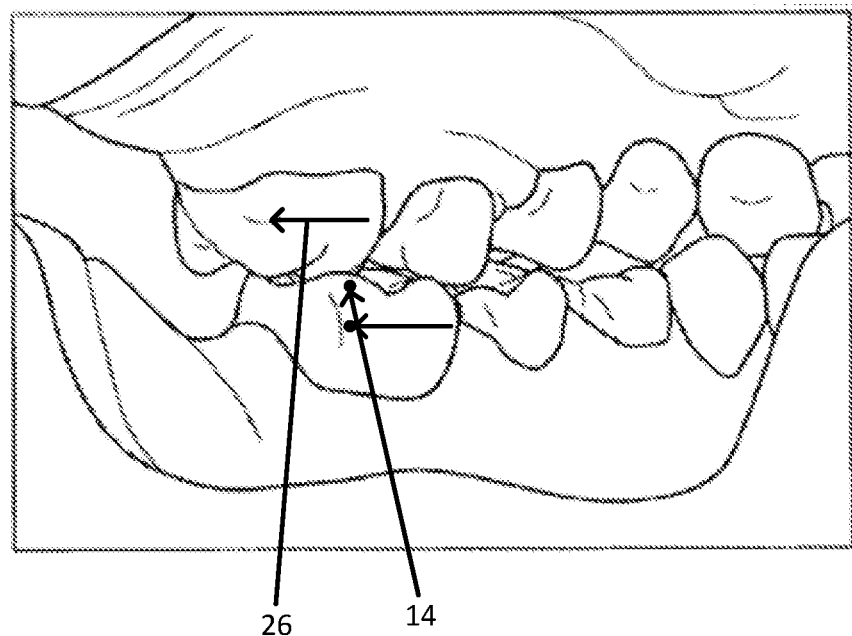
FIGS. 5a, 5b show a view of the left half of the jaw from dorsal both in the phase of the closing of the jaw (FIG. 5a) and in the closed position (FIG. 5b)
Figure 5B:
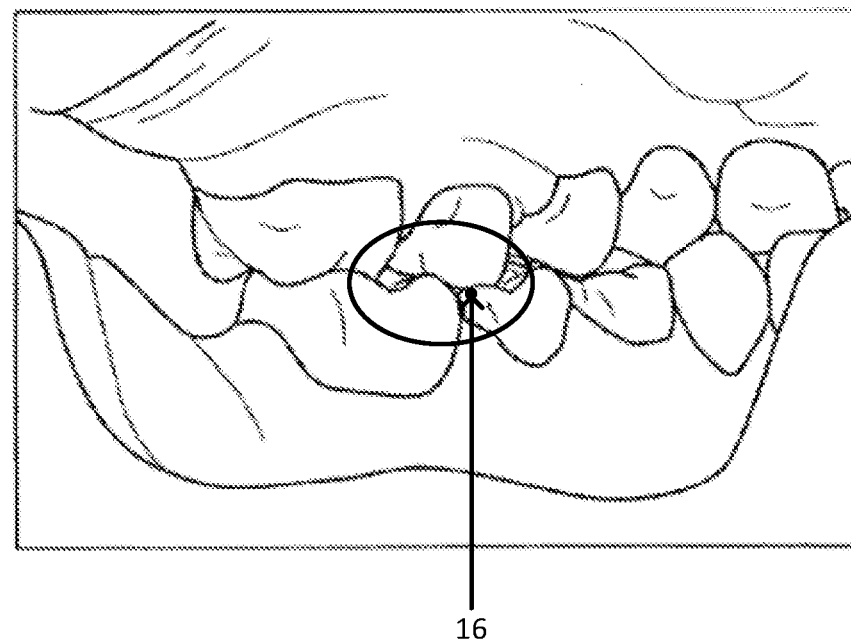

Through the clear occlusal structure, the effective occlusion, and expansion spaces that have been incorporated in a targeted manner, the posterior teeth can be easily and clearly established mutually. In addition, in the context of the invention, the teeth of the tooth replacement are fitted with natural occlusal surface dimensions. Here, the following features of teeth according to the invention are of particular importance:

a. Retrusion path (12, FIG. 2*c*, 26, FIG. 5*a*)
b. Smooth transition from the fissure guidance in the cusp gradients (all degrees of freedom)
c. Protrusion path
d. Strongest support
e. Replacement tooth compliant
f. Stepped tooth neck
g. Approximal/interproximal contact surfaces
h. Functional alignment of the lock
i. Improved level of the central contacts
j. Special cusp slope In the appended claims and the following explanation of the invention use is made of the following definitions:

Lingual cusps: include "inner cusps" of both the upper and the lower jaw, i.e. lingual and palatal cusps Buccal cusps: include "outer cusps" of both the upper and the lower jaw Transverse plane: sectional plane perpendicular to the tooth axis Frontal plane: sectional plane parallel to the tooth axis which runs perpendicular to the mesio-distal axis of the tooth Sagittal plane: sectional plane running parallel to the tooth axis and in mesio-distal direction through the tooth Posterior tooth: molar or premolar The invention is based on the finding that an iatrogenic prosthetic occlusion after incorrect bite produces an eccentric, i.e., destabilizing condyle position or condyle displacement. For example, it was recognized that an incorrect movement pattern, with the ultimate goal of maximum occlusion, is at the expense of the temporomandibular joint, which cannot keep its own position rather leaves its position to adapt to the system.

In the context of the invention, "the neuronal contact position" on the tooth is the starting point and the endpoint for the expansion spaces that have been incorporated in a targeted manner in the movement (the course of the occlusion (30, 32, 34, FIGS. 8*a*-8*c*, see also FIGS. 8*d*-8*e*)). All movements on the occlusal surfaces are gently for the guidance of the temporomandibular joint in a physiological position out of an effective central ICP and mean relief for the entire system, including the joints.

The tooth replacement according to the invention allows all occlusion movements (14, 16, FIGS. 5*a* and 5*b*) to be performed perfectly. Here, use is made of the finding that the centric jaw relation, i.e., the physiological mapping of the lower jaw to the upper jaw, is critical in all areas of prosthetics and has a central importance for the success of the prosthetic restoration.

The tooth replacement according to the invention secures this physiological position of the temporomandibular joints in the ICP and thus of the stomatognathic system as a whole. The keys (right and left temporomandibular joints) find their correct occlusion position, fixed by the occlusal lock to the correct functional posterior teeth (FT). In the temporomandibular joint in conjunction with the neuromuscular system these will hold the keys in their desired position (physiological position).

In the occlusal relief design of denture teeth, it is important not to reach a keyed point-to-point toothing, but to provide the patient through a small sliding clearance in the sense of a dynamic occlusion the possibility of neuromuscular setting of his programmed physiological temporomandibular joint centric.

The specifications for the design of tooth replacement according to the invention were formed using an additive wax-up technique in a fully adjustable articulator "type Protar". Provisos from scientific studies have been empirically implemented in a waxed mold and following first tests to verify the required functional freedoms of the quadrants digitized in the laboratory and milled from PMMA plastic. This process allows the optimization of the occlusal surfaces according to scientific principles. In this context, a good centric allocation of jaw halves contributes to fixing a healthy temporomandibular joint position.

In the context of the invention, in spite of all freedom, the closed rows of teeth provide secure centric support of the rows of teeth against each other. The view onto the right jaw halves from dorsal clearly shows that both in the phase of the closing of the jaw as well as mediotrusion movements the denture teeth function unimpededly.

The tooth replacement according to the invention was developed with the goal of dynamic occlusal guidance in order to improve masticatory performance, stabilization of the prostheses, pleasant wearing comfort and reducing the risk of pressure sores, whereupon the special occlusion concept has emerged. The movements on the tooth replacement according to the invention run smoothly without interruptions, with correct setup information without grinding off, very evenly, both on the right and on the side. It is possible to make restorations that are at maximum level in term of functionality and aesthetics.

The tooth replacement according to the invention was obtained by the development and use of a system for measurement of jaw movements. A tooth replacement was created taking into account these scientific findings. Scientific provisos have been empirically implemented in a waxed mold and following first tests to verify the required functional freedoms of the quadrants digitized in the laboratory and milled from PMMA plastic. Using these prototypes measurements and tests have been performed and documented in a scientific experiment addressing the question of functionality in terms of the findings described. The data and facts gained therefrom had an influence on a revision of the prototype and were then checked again. In doing so, the optimization according to the invention of the occlusal surfaces was achieved according to scientific criteria.

According to a further aspect of the invention, the tooth replacement has at least two adjacently arranged teeth, especially posterior teeth, of which one having a mesial contact surface can be contacted with a distal contact surface of another tooth, characterized in that the mesial (distal) contact surface is curved convexly in a calotte-like or spherical manner, thus having a convex edge both in a sagittal plane and in a transverse plane, and the distal (mesial) contact surface is curved concavely spherically for producing a form-fit contact with the convexly curved contact surface, thus having a concave edge both in a sagittal plane and in a transverse plane.

Figure 6B:
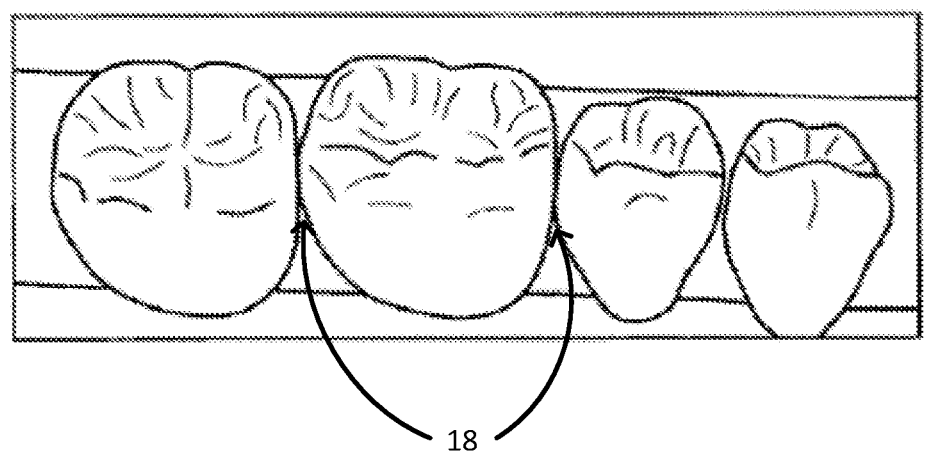

The mesial and distal contact areas that can be contacted are designed have the shape of a spherical shell segment, so as to ensure form-fit contact to one another in all tooth positions. On the one hand, this enables the adaptation of the tooth replacement to the particular anatomy of the patient, on the other hand it produces a form-fit contact between adjacent teeth in the area of the mesial and distal contact surfaces (22, FIG. 6*a*, 18, FIG. 6*b*) in all teeth positions, so that the desired anatomically predetermined position of the teeth can be reliably obtained. The loosening of individual teeth in a plastic support which is occasionally observed in conventional tooth replacements is reliably excluded by the development of the mesial and distal contact surfaces according to the invention.

In this context it has proved to be particularly advantageous if the radius of curvature of the convexly curved contact surface, which preferably is the mesial contact surface, is approximately equal to the radius of curvature of the concavely curved contact surface, said concave contact surface (18, FIG. 6*b*) being preferably formed by the distal contact surface.

Surprisingly, it has been found that the best possible anchorage of the teeth in the base material is achieved when the tooth neck of at least one tooth is stepped in such a way that between crown and root a recessed shoulder is formed. Therefore, the tooth cross-section decreases stepwise, starting from the tooth crown in the direction of the tooth root in the area of the tooth neck. The lower retention with laterally acting forces caused by the stepwise reduction of the cross section is more than offset, surprisingly, by the support of the transition from tooth crown to the tooth root in the tooth area in the area of the steps, so that overall improved anchorage of the tooth in the base material is obtained. In addition, the translucence of the tooth necks through the plastic support is prevented by the stepped tooth neck.

In the context of the invention a recessed shoulder between the tooth crown and tooth root is understood to be a shoulder, which is constituted that to a connection line between a boundary surface of the tooth root and the tooth crown in the area of the tooth neck extends outside of the tooth body.

A particularly reliable retention of the replacement teeth in the support material is achieved, when the shoulder between tooth crown and tooth root is implemented revolving around the entire periphery of the tooth, so that in the area of the transition between tooth crown and tooth root a circumferential contact face of the tooth is formed on the support material.

The invention can be used particular advantageously with entire replacement teeth. The variability described in the adaptation of replacement teeth to the anatomical conditions of the patient can, however, already be achieved if crowns of adjacent teeth are implemented with approximal contact surfaces, of which one is convexly curved and the other is concavely curved for producing a form-fit contact. The shape of the approximal contact surfaces for a tooth replacement according to the invention is optimized for a form-fit contact and thus increased in comparison to the approximal contact areas of natural teeth.

The circularly stepped dental neck used in a preferred embodiment of the invention improves the fixing in the base and facilitates papillae design.

Hereinafter, the invention will be explained with reference to the drawing to which express reference is made in respect of all details essential to the invention and which were not emphasized in more detail in the description.

The design of the occlusal surfaces of the posterior teeth of the tooth replacement according to the invention is illustrated particularly well in FIGS. 2*a*-2*e*, 6*a*-6*b* and 9*a*-9*h*.

The following features indicated in the claims are presented in the figures: The fissure base is only relatively slightly curved. This results in a smooth transition between gradients and central fissure. In addition, the base of the tooth pit is only relatively slightly curved.

The occlusal surfaces are continuously concavely curved in a frontal plane passing through the cusps starting from the first gradient through the central fissure to the second gradient. In other words, the central fissure has no convex portions, so that in occlusion position no keyed point-to-point toothing is obtained, rather the patient is provided through a small sliding clearance in the sense of a dynamic occlusion the possibility of neuromuscular setting of his temporomandibular joint centric.

Furthermore, the gradients have no areas with steep slopes in the direction of the cusp tips. This leads to a dynamic occlusion in laterotrusion movements.

The central fissure has a minimum depth over the full tooth width. This leads to a dynamic occlusion in protrusion and retrusion. On the other hand, the pit is not particularly deep in relation to the tooth width, which leads to the unimpeded functioning of the replacement teeth. The deepest point of the tooth pit is not the point of greatest curvature of the pit. In other words, the tooth pit is flat at the bottom. This facilitates dynamic sliding movement starting from the occlusion position.

Figure 7:
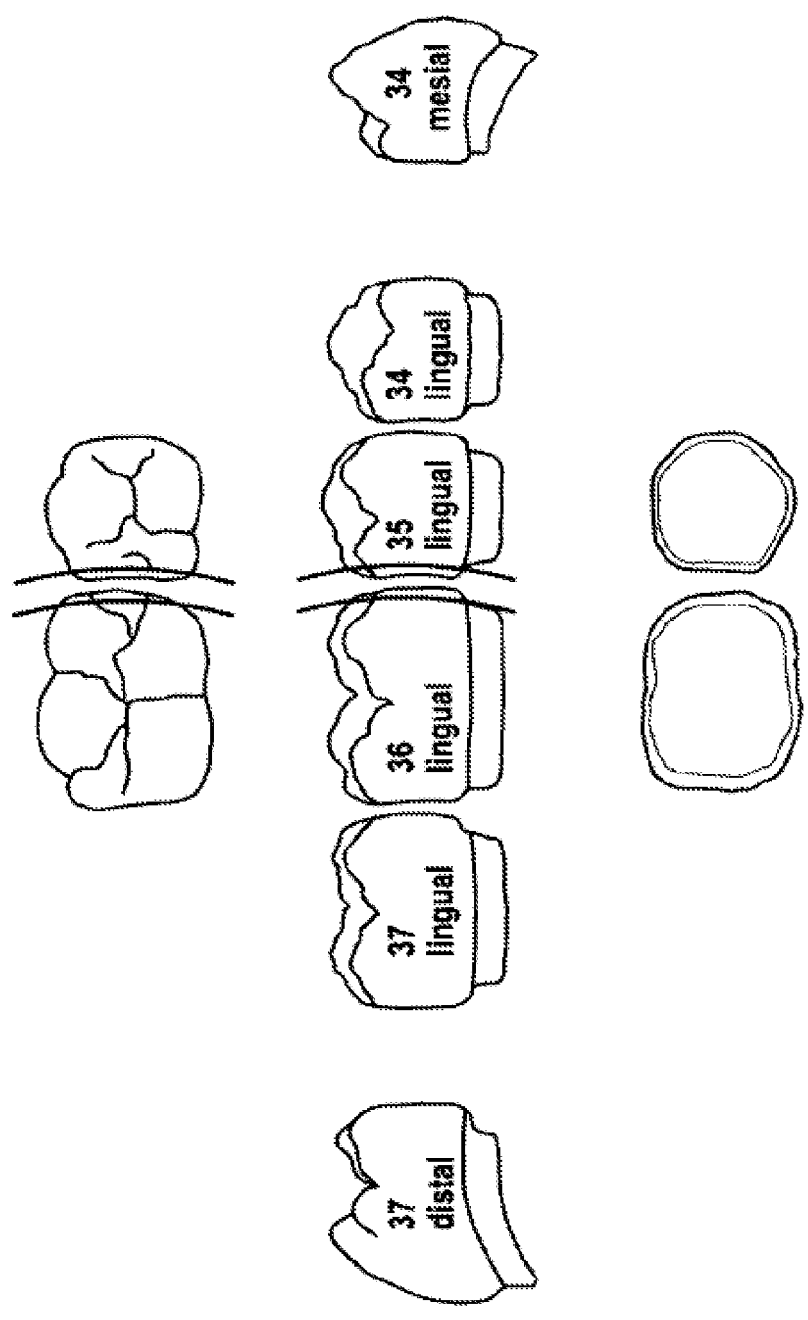
FIG. 7 shows an occlusal view, a lingual view and a basal view of a tooth replacement according to the invention implemented in the form of a row of teeth (second embodiment)
Figure 8A:
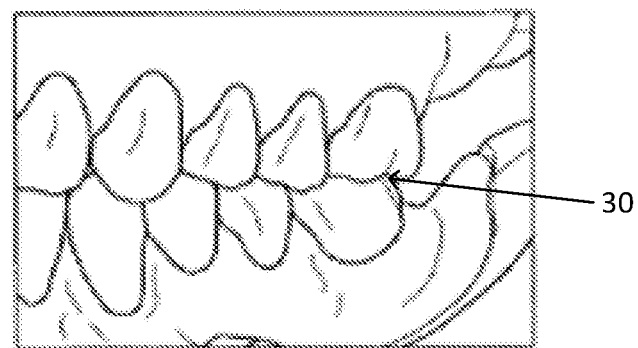
FIGS. 8a, 8b, 8c, 8d, 8e show further side views of the first embodiment of the tooth replacement according to the invention.
Figure 8B:
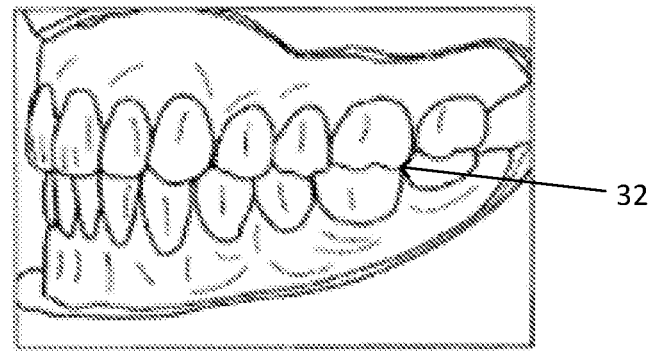
Figure 8C:
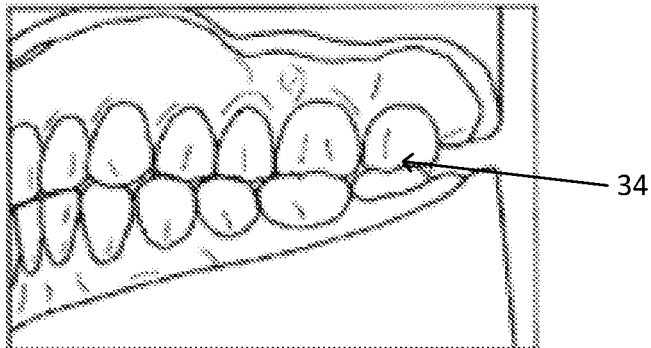
Figure 8D:
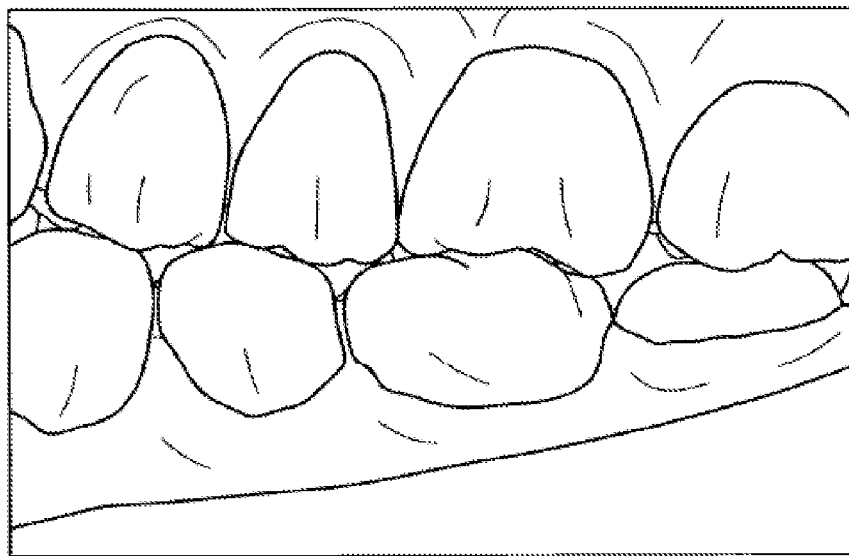
Figure 8E:
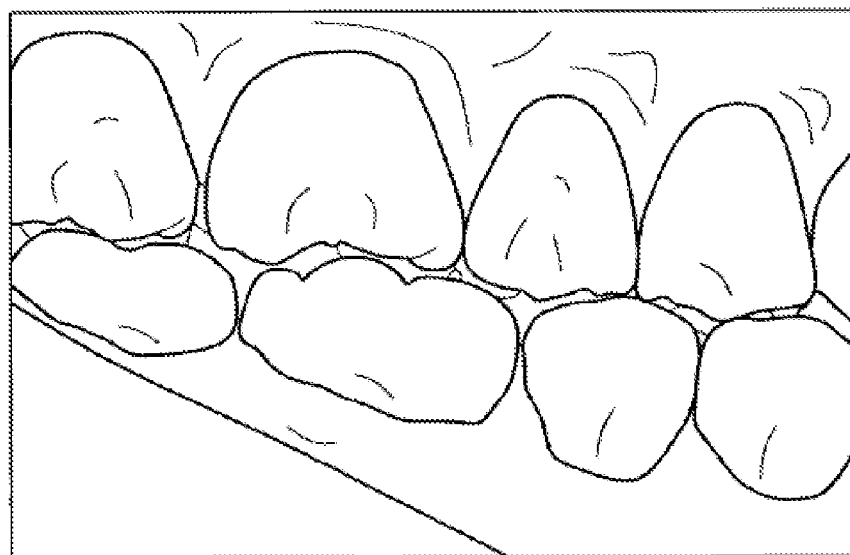

FIG. 7 shows particularly clearly that the mesial contact surface of tooth 36 is implemented curved convexly so that it fits form-fit to the distal contact surface of tooth 35. All teeth of the row of teeth of FIG. 7 have a circumferentially stepped tooth neck, so that the tooth cross-section decreases stepwise, starting from the tooth crown in the direction of the tooth root in a shoulder implemented in the area of the tooth neck.

What is claimed is:

1. A tooth replacement comprising at least two adjacent posterior teeth comprising a first tooth and a second tooth adjacent to the first tooth, wherein each of the first and second teeth include a mesial contact surface, a distal contact surface, and an occlusal surface, wherein the occlusal surface comprises a least one buccal cusp having a buccal cusp tip, a lingual cusp having a lingual cusp tip, a central fissure which has at least one tooth pit and passes through the occlusal surface in a mesiodistal direction between the two cusps, a first gradient which slopes downward from the buccal cusp tip in a direction of the central fissure, and a second gradient which slopes downward from the lingual cusp tip in the direction of the central fissure, wherein the occlusal contact surface comprise expansion spaces to obtain a dynamic occlusal guidance, wherein the tooth pits of the occlusal surfaces of the first and second posterior teeth engage in an occlusion position with respective antagonists of the posterior teeth, wherein the respective antagonist teeth include a further occlusal surface having at least one further cusp, to engage in the occlusion position with the tooth pit of the occlusal surface of the posterior teeth, wherein a length of a retrusion path starting from the occlusion position is at least 0.6 mm, wherein the mesial contact surface of the first tooth is curved in a calotte-like or spherical manner, having a convex edge both in a sagittal plane and in a transverse plane, and wherein the second tooth has a distal contact surface abutting the mesial contact surface of the first tooth, wherein the distal contact surface of the second tooth is curved concavely spherically for producing a form-fit contact with a convexly curved mesial contact surface of the first tooth, thus having a concave edge both in a sagittal plane and in a transverse plane, wherein a radius of a curvature of the mesial contact surface of the first tooth is approximately equal to a radius of a curvature of the distal contact surface of the second tooth, wherein a radius of curvature of the occlusal surface of at least one of the posterior teeth as a base of the tooth pit is sectional planes running parallel to a tooth axis through the base of the tooth pit is greater than 1.2 mm and less than 5 mm.

2. The tooth replacement according to claim 1, characterized in that the expansion spaces are implemented as profilings extending in a normal direction to a tangent plane of the distal contact surface, the mesial contact surface or the occlusal surface of at least one of the posterior teeth.

3. The tooth replacement according to claim 1, characterized in that in a frontal plane passing through the central fissure the radius of the curvature of the occlusal surface at the base of the central fissure is greater than one quarter of a distance between the two cusp tips of at least one of the posterior teeth, resulting in a smooth transition between the first gradient, the central fissure and the second gradient.

4. The tooth replacement according to claim 1, characterized in that the occlusal surface of one of the posterior teeth is continuously concavely curved in a frontal plane passing through the cusps starting from the first gradient through the central fissure to the second gradient.

5. The tooth replacement according to claim 1, characterized in that in all frontal planes passing through the central fissure, the maximum slope angle of the first or of the second gradient with respect to a transverse plane is less than 40°, and more than 20°.

6. The tooth replacement according to claim 1, characterized in that in all frontal planes passing through the central fissure, a distance between the base of the central fissure and the transverse plane passing through the highest cusp tip is greater than 0.3 mm and smaller than 1.5 mm.

7. The tooth replacement according to claim 1, characterized in that a distance between the two cusp tips is more than 4 times and less than 15 times, than a distance between a transverse plane passing through the base of the tooth pit and a transverse plane passing through the highest cusp.

8. The tooth replacement according to claim 1, characterized in that in a frontal plane passing through the base of the tooth pit the radius of the curvature of the occlusal surface increases at least section-wise starting from a base of the tooth pit in a direction towards an edge of the tooth pit of at least one of the two posterior teeth.

9. The tooth replacement according to claim 1, wherein a length of a protrusion path is 0.4 mm to 0.6 mm.

10. The tooth replacement according to claim 1, characterized in that in the occlusion position the cusp of antagonist contacts the occlusal surface of at least one of the posterior teeth in the area of the tooth pit in a planar manner, wherein the contact surface is more than 0.5 mm2 and less than 3 mm2.

11. The tooth replacement according to claim 1, characterized in that the radius of the curvature of the convexly curved contact surface of the first tooth corresponds approximately to the radius of the curvature of the concavely curved further contact surface of the second tooth.

12. The tooth replacement according to claim 1, characterized in that a tooth neck of at least one of the posterior teeth is offset such that between a tooth crown and a tooth root a recessed shoulder is formed, said shoulder revolving around a periphery of the posterior tooth.

13. The tooth replacement according to claim 1, comprising at least two adjacently arranged teeth, especially molars or premolars, of which one having a mesial contact surface that is contactable with a distal contact surface of another tooth, characterized in that the mesial or distal contact surface is curved convexly in a calotte-like or spherical manner, having a convex edge in a sagittal plane and in a transverse plane, and the distal or mesial contact surface is curved concavely spherically for producing a form-fit contact with the convexly curved contact surface, having a concave edge in a sagittal plane and in a transverse plane.

14. The tooth replacement according to claim 13, characterized in that the radius of the curvature of the convexly curved contact surface corresponds approximately to the radius of the curvature of the concavely curved contact surface.

15. The tooth replacement according to claim 1, characterized in that a tooth neck of at least one tooth is offset such that between a tooth crown and a tooth root a recessed shoulder is formed.

16. The tooth replacement according to claim 15, characterized in that the shoulder is implemented revolving around a periphery of the tooth.

17. The tooth replacement according to claim 1, characterized by an antagonist to one of the teeth, wherein the length of a retrusion path from the tooth pit is 0.6 mm to 0.8 mm or the length of a protrusion path from a neuronal contact position is 0.4 mm to 0.6 mm.

* * * * *

UNITED STATES PATENT AND TRADEMARK OFFICE
CERTIFICATE OF CORRECTION

| | | |
|---|---|---|
| PATENT NO. | : 10,456,226 B2 | Page 1 of 1 |
| APPLICATION NO. | : 15/596554 | |
| DATED | : October 29, 2019 | |
| INVENTOR(S) | : Wolfgang Arnold et al. | |

It is certified that error appears in the above-identified patent and that said Letters Patent is hereby corrected as shown below:

On the Title Page

Item (73) "… KUZLER" should read -- … KULZER --

Signed and Sealed this
Seventeenth Day of May, 2022

Katherine Kelly Vidal
*Director of the United States Patent and Trademark Office*